(12) United States Patent
Saevecke et al.

(10) Patent No.: US 11,311,428 B2
(45) Date of Patent: Apr. 26, 2022

(54) ABSORBENT ARTICLE HAVING A NONWOVEN MATERIAL WITH ANTIMONY-FREE POLYETHYLENE TEREPHTHALATE

(71) Applicant: The Procter & Gamble Company, Cincinnati, OH (US)

(72) Inventors: Dirk Saevecke, Schwalbach am Taunus (DE); Otto Virtanen, Schwalbach am Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 776 days.

(21) Appl. No.: 16/132,513

(22) Filed: Sep. 17, 2018

(65) Prior Publication Data

US 2019/0105424 A1    Apr. 11, 2019

(30) Foreign Application Priority Data

Oct. 6, 2017   (EP) ..................................... 17195227

(51) Int. Cl.
*A61F 13/511*    (2006.01)
*A61L 15/22*    (2006.01)
(Continued)

(52) U.S. Cl.
CPC .... *A61F 13/5116* (2013.01); *A61F 13/51474* (2013.01); *A61F 13/537* (2013.01);
(Continued)

(58) Field of Classification Search
CPC ...... A61F 13/47; A61F 13/49; A61F 13/5116; A61F 13/51474; A61F 13/515; A61F 13/537; A61F 13/53743; A61F 13/53747; A61F 2013/15463; A61F 2013/4708; A61F 2013/51452; A61F 2013/530496;
(Continued)

(56) References Cited

U.S. PATENT DOCUMENTS 5,053,482 A    10/1991   Tietz
5,171,308 A    12/1992   Gallagher et al.
(Continued)

FOREIGN PATENT DOCUMENTS

CN    101327156 A    12/2008
CN    101381453 A    3/2009
(Continued)

OTHER PUBLICATIONS

Extended European Search Report and Search Opinion; Application No. 17195227.8; dated Feb. 16, 2018, 6 pages.
(Continued)

*Primary Examiner* — Susan S Su
(74) *Attorney, Agent, or Firm* — Daniel S. Albrecht; Christian M. Best

(57) ABSTRACT

The present disclosure relates to absorbent articles comprising a nonwoven material, the nonwoven material comprising PET resin having less than 150 ppm of antimony. One or more layers of cover materials are covering the nonwoven material both on the wearer-facing surface and on the garment-facing surface, such that the nonwoven material does not form a wearer-facing or garment-facing surface of the absorbent article.

18 Claims, 2 Drawing Sheets

(51) Int. Cl.
*A61F 13/537* (2006.01)
*A61L 15/26* (2006.01)
*D04H 3/011* (2012.01)
*A61L 15/60* (2006.01)
*D04H 1/435* (2012.01)
*A61F 13/514* (2006.01)
*A61F 13/515* (2006.01)
*A61F 13/53* (2006.01)

(52) U.S. Cl.
CPC .. *A61F 13/53743* (2013.01); *A61F 13/53747* (2013.01); *A61L 15/225* (2013.01); *A61L 15/26* (2013.01); *A61L 15/60* (2013.01); *D04H 1/435* (2013.01); *D04H 3/011* (2013.01); *A61F 13/515* (2013.01); *A61F 2013/51452* (2013.01); *A61F 2013/530496* (2013.01)

(58) Field of Classification Search
CPC ........ A61L 15/225; A61L 15/26; A61L 15/60; D04H 1/435; D04H 3/011
USPC .................................. 604/358–392
See application file for complete search history.

(56) References Cited

U.S. PATENT DOCUMENTS

| | | | |
|---|---|---|---|
| 5,171,309 A * | 12/1992 | Gallagher | A61F 13/15252 220/DIG. 30 |
| 6,034,202 A | 3/2000 | Aharoni et al. | |
| 7,144,974 B2 | 12/2006 | Honda et al. | |
| 7,371,701 B2 | 5/2008 | Inagaki | |
| 8,759,606 B2 | 6/2014 | Bond et al. | |
| 2005/0027267 A1* | 2/2005 | Van Dyke | A61F 13/53713 604/367 |
| 2006/0004337 A1* | 1/2006 | Datta | A61F 13/5638 604/385.01 |
| 2006/0057373 A1 | 3/2006 | Inagaki et al. | |
| 2015/0065973 A1 | 3/2015 | Roe et al. | |
| 2015/0112293 A1* | 4/2015 | Gust | B32B 38/145 604/385.01 |
| 2015/0337496 A1 | 11/2015 | Lee | |
| 2016/0074249 A1* | 3/2016 | Rosati | A61F 13/15203 604/378 |
| 2017/0259550 A1 | 9/2017 | Neton et al. | |
| 2017/0260689 A1 | 9/2017 | Kramkowski et al. | |

FOREIGN PATENT DOCUMENTS

| | | |
|---|---|---|
| CN | 102341081 A | 2/2012 |
| CN | 104470482 A | 3/2015 |
| DE | 202015005969 U1 | 11/2015 |
| WO | WO 2014/146587 A1 | 9/2014 |

OTHER PUBLICATIONS

Search Report and Written Opinion for PCT/US2018/053681 dated Nov. 19, 2018.
U.S. Appl. No. 16/132,516, filed Sep. 17, 2018, Saevecke et al.
U.S. Appl. No. 16/132,523, filed Sep. 17, 2018, Saevecke et al.
All Office Actions; U.S. Appl. No. 16/132,516, filed Sep. 17, 2018.
All Office Actions; U.S. Appl. No. 16/132,523, filed Sep. 17, 2018.

* cited by examiner

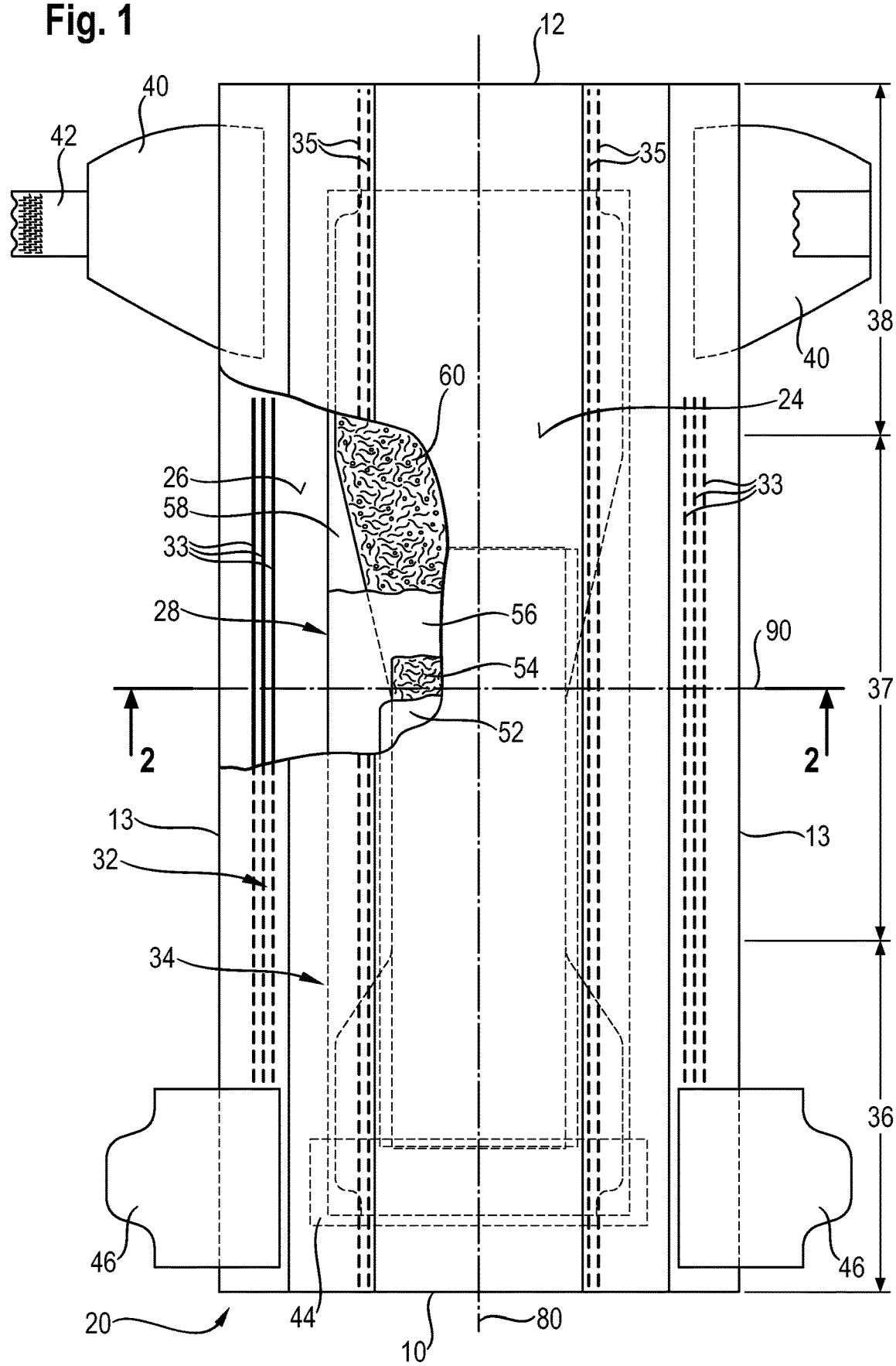

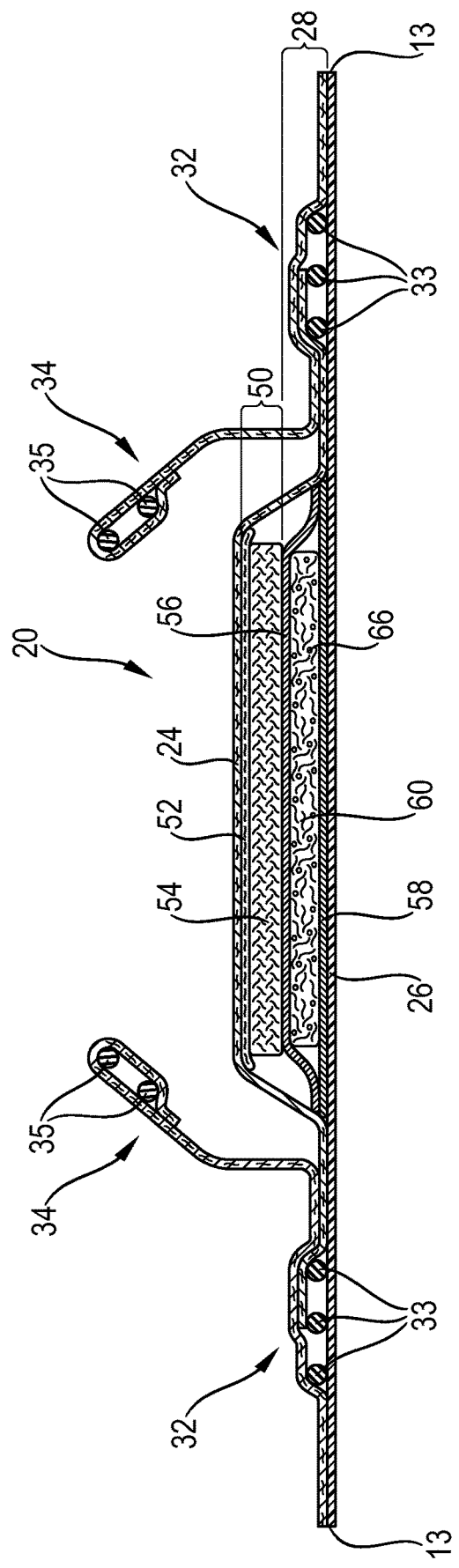

ABSORBENT ARTICLE HAVING A NONWOVEN MATERIAL WITH ANTIMONY-FREE POLYETHYLENE TEREPHTHALATE

CROSS REFERENCE TO RELATED APPLICATION

This application claims priority under 35 U.S.C. § 119, to European Patent Application Serial No. 17195227.8, filed on Oct. 6, 2017, the entire disclosure of which is hereby incorporated by reference.

FIELD

The present disclosure provides an absorbent article for personal hygiene such as a diaper or pant (for babies, toddlers or adults), a training pant, or a feminine hygiene sanitary napkin. The absorbent article comprises a nonwoven material, such as a nonwoven web. The nonwoven material comprises PET resin comprised by at least a part of the fibers of the nonwoven material (i.e. not all fibers in the material need to comprise PET resin), wherein the PET has less than 150 ppm of antimony. One or more layers of cover materials are covering the nonwoven material both on the wearer-facing surface and on the garment-facing surface, such that the nonwoven material does not form a wearer- or garment facing surface of the absorbent article.

BACKGROUND

Polyethylene terephthalate (PET) is a well known and widely used material. The majority of the world's production of PET is for synthetic fibers (in excess of 60%), with bottle production accounting for about 30% of global demand. In the context of textile applications, PET is typically referred to by its common name, polyester.

PET is also often used in absorbent articles: Many absorbent articles, such as diapers, pants and feminine hygiene articles, comprise one or more nonwoven webs which comprise polyethylene terephthalate (PET).

PET is industrially produced by esterification or transesterification of terephthalic acid or dimethyl terephthalate and ethylene glycol to produce bis(2-hydroxyethyl) terephthalate which is then subjected to polycondensation at high temperatures in vacuo in the presence of a catalyst. As a conventional polyester polymerization catalyst used in polycondensation of polyester, antimony trioxide.

As a consequence of the use of an antimony compound as catalyst, traces of the antimony can be found in the PET resin and thus, also in the nonwoven web comprised by the absorbent article. Trace amounts of antimony in PET are typically in the range of 200 to 300 ppm.

Antimony is reported to have a negative impact on the environment and carcinogenic potential. Though the typical amounts of antimony in the PET resin are extremely low and not considered to be critical, increased attention on this chemical compound has been raised by consumers.

PET resin made by a process, which uses a catalyst other than antimony compounds, is known in the art, for example in CA02420958 assigned to Toyo Boseki Kabushiki Kaisha, JP; EP1316585B1 assigned to Invista Technologies, CH; EP1491572A1 assigned to Toray Industries, Inc, JP; EP1153953B1 and EP1327648A1, both assigned to Toyo Boseki Kabushiki Kaisha, JP; For example, a known approach to PET resin processing technology is to implement a titanium-containing polycondensation catalyst as a replacement for the conventional antimony-containing polycondensation catalyst. However, such titanium-containing polycondensation catalyst typically gives a yellowish color to the resultant PET resin, rendering the PET polyester fiber manufactured therefrom less commercially desired due to its yellowish look.

To reduce the yellowish look, it has been suggested to add a phosphorus stabilizer during the PET resin process in order to reduce the yellowish look of the PET resin caused by the titanium-containing polycondensation catalyst. For instance, U.S. Patent Application Publication US 2006/0014920A1 assigned to Teijin Fibers discloses a mixture-based catalyst mixed by tetrabutyltitanate (TBT), product of reaction of TBT and trimellitic anhydride, and triethyl phosphonoacetate (TEPA).

Though antimony free PET has been disclosed in the prior art, to date it has not found wide use in the industry, as most commercially available antimony free PET resins still have a yellowish color.

In absorbent articles, the use of antimony free PET has not been suggested so far. One of the reasons is supposed to be related to the yellowish color, which consumers perceive as low quality. This appears to be specifically critical as absorbent articles get into direct contact with the delicate skin, especially the skin of babies and toddlers.

SUMMARY

Absorbent article comprising a topsheet forming a wearer-facing surface of the absorbent article, a backsheet forming a garment-facing surface of the absorbent article and an absorbent core interposed between the topsheet and the backsheet, wherein the absorbent article comprises a nonwoven material, such as a nonwoven web, the nonwoven material:
  comprising at least 10%, by weight of the nonwoven material, of polyethylene terephthalate (PET), the PET comprising less than 150 ppm of antimony; and
  having an a* value unequal zero; and
  having a b* value unequal zero; and
  being covered by one or more first cover layer(s) towards the wearer-facing surface of the absorbent article, the one or more first cover layer(s) comprising or consisting of the topsheet, such that the nonwoven material does not form the wearer-facing surface of the absorbent article; and
  being covered by one or more second layer(s) towards the garment-facing surface of the absorbent article, the one or more first layer(s) comprising or consisting of the backsheet, such that the nonwoven material does not form the garment-facing surface of the absorbent article.

The nonwoven material may be a nonwoven web. Alternatively, the nonwoven material may be fibers which are comprised by a component of the absorbent article, such as the absorbent core, without being in the form of a web.

The nonwoven material may comprise at least 30%, or at least 50%, or at least 70%, or 100%, by weight of the material, of PET.

The PET comprised by the nonwoven material may have less than 100 ppm, less than 75 ppm, less than 50 ppm, less than 10 ppm of antimony, or may be completely antimony-free (i.e. 0 ppm of antimony).

The antimony content of the PET may be measured by microwave digestion of the PET resin under pressure ($HNO_3$ and HCL) and subsequent determination of antimony by Inductively coupled plasma mass spectrometry (ICP-MS).

Determination of antimony content in PET can, for example, be done by GALAB Laboratories GmbH, Hamburg; Germany Measuring the antimony content in the PET in accordance with ISO 105 E04, which uses less harsh digestion methods and Artificial Acid Sweat Solution, may not lead to determination of the complete antimony content in the PET, so this method should not be followed for the present disclosure.

The a* value of the nonwoven material may be less than −0.6, or less than −0.7, or from −2.0 to −0.6, or from −1.5 to −0.7, or from −1.5 to −0.8.

The b* value of the nonwoven material may be higher than 1.5, or higher than 1.8, or from 1.5 to 5.0, or from 1.5 to 3.5.

The delta E* between the nonwoven material alone and the nonwoven material when being covered by being covered by one or more first cover layer(s) towards the wearer-facing surface of the absorbent article, the one or more first cover layer(s) comprising or consisting of the topsheet, may be at least 1, or may be at least 2, or may be at least 3, or may be at least 4, or may be at least 5.

The delta E* between the nonwoven material alone and the nonwoven material when being covered by being covered by one or more first cover layer(s) towards the wearer-facing surface of the absorbent article, the one or more first cover layer(s) comprising or consisting of the topsheet, may not be more than 10, or may not be more than 8, or may not be more than 7.5.

The delta E* between the nonwoven material alone and the nonwoven material when being covered by one or more second cover layer(s) towards the garment-facing surface of the absorbent article, the one or more second cover layer(s) comprising or consisting of the backsheet, may be at least 1, or may be at least 2, or may be at least 3, or may be at least 4, or may be at least 5.

The delta E* between the nonwoven material alone and the nonwoven material when being covered by being covered by one or more second cover layer(s) towards the garment-facing surface of the absorbent article, the one or more second cover layer(s) comprising or consisting of the backsheet, may not be more than 10, or may not be more than 8, or may not be more than 7.5.

The one or more first cover layer(s) covering the nonwoven material towards the wearer-facing surface may have an opacity of at least 10%, or at least 20%, or at least 30% or at least 40%, wherein, for more than one first cover layer, the opacity is combined opacity of the one or more first cover layer(s) covering the nonwoven material towards the wearer-facing surface. The opacity of the one or more first cover layer(s) covering the nonwoven material towards the wearer-facing surface may not be more than 80%, or not be more than 70%, or not be more than 60%, or not be more than 50%, wherein, for more than one first cover layer, the opacity is combined opacity of the one or more first cover layer(s) covering the nonwoven material towards the wearer-facing surface.

The topsheet may be an apertured topsheet. The apertured topsheet may be an apertured nonwoven fabric. The total open area of the apertured topsheet may be from 15% to 40%, or from 15% to 35%, or from 20% to 35%. The size of the apertures may be from 2.0 mm$^2$ to 6 mm$^2$; or from 2 mm$^2$ to 5 mm$^2$; or from 2.5 mm$^2$ to 5 mm$^2$; or from 3 mm$^2$ to 5 mm$^2$.

Alternatively, the topsheet—and the one or more other first cover layers which may cover the nonwoven material comprising PET with less than 150 ppm of antimony towards the wearer-facing surface—are non-apertured.

Also, the backsheet—and the one or more other second cover layers which may cover the nonwoven material comprising PET with less than 150 ppm of antimony towards the garment-facing surface—are non-apertured.

The one or more second cover layer(s) covering the nonwoven material towards the garment-facing surface have an opacity of at least 10%, or at least 20%, or at least 30% or at least 40%, wherein, for more than one second cover layer, the opacity is combined opacity of the one or more second cover layer(s) covering the nonwoven material towards the garment-facing surface. The opacity of the one or more second cover layer(s) covering the nonwoven material towards the garment-facing surface may not be more than 80%, or not be more than 70%, or not be more than 60%, or not be more than 50%, wherein, for more than one second cover layer, the opacity is combined opacity of the one or more second cover layer(s) covering the nonwoven material towards the garment-facing surface.

The basis weight of the one or more first cover layer(s) may be at least 10 g/m$^2$, or from 10 g/m$^2$ to 1500 g/m$^2$ (as one of the first cover layers may be the absorbent core). For more than one first cover layers, the basis weight is the combined basis weight of all first cover layers. If the nonwoven material with PET having less than 150 ppm of antimony is covered by only one first cover layer (the topsheet) towards the wearer-facing surface, the basis weight of this first cover layer (the topsheet) may be from 10 g/m$^2$ to 50 g/m$^2$, or from 10 g/m$^2$ to 30 g/m$^2$. If the nonwoven material with PET having less than 150 ppm of antimony is covered by more than one first cover layer, the combined basis weight of these first cover layers may be from 30 g/m$^2$ to 150 g/m$^2$, or from 30 g/m$^2$ to 1000 g/m$^2$, or from 30 g/m$^2$ to 800 g/m$^2$ (inter alia depending on the number of first cover layers).

The basis weight of the one or more second cover layer(s) may be at least 10 g/m$^2$, or from 10 g/m$^2$ to 1500 g/m$^2$ (as one of the second cover layers may be the absorbent core). For more than one second cover layers, the basis weight is the combined basis weight of all second cover layers. If the nonwoven material with PET having less than 150 ppm of antimony is covered by only one second cover layer (the backsheet) towards the garment-facing surface, the basis weight of this second cover layer (the backsheet) may be from 10 g/m$^2$ to 80 g/m$^2$, or from 10 g/m$^2$ to 60 g/m$^2$. If the nonwoven material with PET having less than 150 ppm of antimony is covered by more than one second cover layer, the combined basis weight of these second cover layers may be from 30 g/m$^2$ to 1500 g/m$^2$, or from 30 g/m$^2$ to 1000 g/m$^2$, or from 30 g/m$^2$ to 800 g/m$^2$ (inter alia depending on the number of first cover layers).

The one or more first and second cover layer(s) can be made of any material suitable for use in an absorbent article, such as, but not limited to, nonwoven materials (e.g. nonwoven webs), woven materials, knitted materials, films, foams, compounds of non-consolidated fibers, such as layers of cellulose fibers, a layer of modified cellulose fibers (e.g. inter-fiber cross-linked cellulose fibers), natural fibers, synthetic fibers, superabsorbent polymer particles, or combinations of any such materials.

The absorbent core of the absorbent article may comprise a combination of cellulose fibers and superabsorbent polymer particles, and the absorbent core may comprise areas which are free of cellulose fibers and superabsorbent polymer particles. The areas being free of cellulose fibers and superabsorbent polymer particles may be elongated areas having a length of from 20% and 80%, or from 20% to 70%, or from 30% to 60%, by total longitudinal dimension of the absorbent article.

BRIEF DESCRIPTION OF THE DRAWINGS

While the specification concludes with claims particularly pointing out and distinctly claiming the present disclosure, it is believed that the same will be better understood from the following description read in conjunction with the accompanying drawings in which:

FIG. 1 is an example absorbent article in the form of a diaper.

FIG. 2 is a transversal cross-section of the diaper of FIG. 1.

DETAILED DESCRIPTION

Definition of Terms

As used herein, "absorbent article" refers to devices that absorb and contain body exudates, and, more specifically, refers to devices that are placed against or in proximity to the body of the wearer to absorb and contain the various exudates discharged from the body. Absorbent articles may include diapers (baby diapers and diapers for adult incontinence), pants (for babies or for adults), absorbent inserts (which are intended to be inserted into an outer cover to form a diaper or pant), feminine care absorbent articles such as sanitary napkins or pantiliners, and the like. As used herein, the term "exudates" includes, but is not limited to, urine, blood, vaginal discharges, sweat and fecal matter. Absorbent articles of the present disclosure may be disposable absorbent articles and may be disposable diapers and disposable pants.

The term "absorbent core" as used herein refers to a component, which is placed or is intended to be placed within an absorbent article and which comprises an absorbent material enclosed in a core wrap. The term "absorbent core" does not include an acquisition or distribution layer or any other component of an absorbent article which is not either an integral part of the core wrap or placed within the core wrap. The absorbent core is typically the component of an absorbent article which comprises all, or at least the majority of, superabsorbent polymer and has the highest absorbent capacity of all the components of the absorbent article.

"Bicomponent" refers to fibers having a cross-section comprising two discrete polymer components, two discrete blends of polymer components, or one discrete polymer component and one discrete blend of polymer components. "Bicomponent fiber" is encompassed within the term "Multicomponent fiber." A bicomponent fiber may have an overall cross section divided into two subsections of the differing components of any shape or arrangement, including, for example, concentric core-and-sheath subsections, eccentric core-and-sheath subsections, side-by-side subsections, radial subsections, etc.

"Color", as used herein, includes any color in the CIELAB color space including primary color, secondary color, tertiary color, the combination thereof, as well as black and white.

CIE L*a*b* ("CIELAB") is the most commonly used color space specified by the International Commission on Illumination (French Commission internationale de l'éclairage, hence its CIE initialism). It describes all the colors visible to the human eye and was created to serve as a device independent model to be used as a reference.

The three coordinates of CIELAB represent the lightness of the color (L*=0 yields black and L*=100 indicates diffuse white; specular white may be higher), its position between red/magenta and green (a*, negative values indicate green while positive values indicate magenta) and its position between yellow and blue (b*, negative values indicate blue and positive values indicate yellow). The asterisk (*) after L, a and b are part of the full name, since they represent L*, a* and b*, to distinguish them from Hunter's L, a, and b.

The term "denier" as used herein refers to a unit used to indicate the fineness of a filament/fiber.

The unit expresses the mass of a filament/fiber in grams per 9000 meters of length.

As used herein, "diaper" and "pant" refers to an absorbent article generally worn by babies, infants and incontinent persons about the lower torso so as to encircle the waist and legs of the wearer and that is specifically adapted to receive and contain urinary and fecal waste. In a pant, as used herein, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be pre-formed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened). In a diaper, the waist opening and leg openings are only formed when the diaper is applied onto a wearer by (releasable) attaching the longitudinal edges of the first and second waist region to each other on both sides by a suitable fastening system.

As used herein, "disposable" is used in its ordinary sense to mean an article that is disposed or discarded after a limited number of usage over varying lengths of time, for example, less than 20 usages, less than 10 usages, less than 5 usages, or less than 2 usages. If the disposable absorbent article is a diaper, a pant, sanitary napkin, sanitary pad or wet wipe for personal hygiene use, the disposable absorbent article is most often intended to be disposed after single use.

"Monocomponent" refers to fiber formed of a single polymer component or single blend of polymer components, as distinguished from bicomponent or multicomponent fiber.

"Multicomponent" refers to fiber having a cross-section comprising two or more discrete polymer components, two or more discrete blends of polymer components, or at least one discrete polymer component and at least one discrete blend of polymer components. "Multicomponent fiber" includes, but is not limited to, "bicomponent fiber." A multicomponent fiber may have an overall cross section divided into subsections of the differing components of any shape or arrangement, including, for example, coaxial subsections, concentric core-and-sheath subsections, eccentric core-and-sheath subsections, side-by-side subsections, islands—in the sea subsection, segmented pie subsections, etc.

A "nonwoven material" is a compilation of nonwoven fibers. The nonwoven material may or may not be in web form, i.e. it may or may not be in the form of a consolidated web which has integrity and is self-sustaining. The fibers which may be comprised by the nonwoven material are the same as those set out below for a nonwoven web.

A "nonwoven web" is a nonwoven material which is a manufactured web of directionally or randomly oriented fibers, consolidated and bonded together, e.g. by one or more patterns of bonds and bond impressions created through localized compression and/or application of heat or ultrasonic energy, or a combination thereof. The fibers may, alternatively or in addition, be consolidated by use of a binder. The binder may be provided in the form of binder fibers (which are subsequently molten) or may be provided in liquid, such as a styrene butadiene binder. A liquid binder is provided to the fibers (e.g. by spraying, printing or foam application) and is subsequently cured to solidify. The term "nonwoven" does not include fabrics which are woven, knitted, or stitch-bonded with yarns or filaments. The fibers may be of natural or man-made origin and may be staple or continuous filaments. Nonwoven fabrics can be formed by many processes such as meltblowing, spunlaid, solvent spinning, electrospinning, and carding. As used herein, "spunlaid" refers to fibers made by spunbond technology without having undergone further processing, such as bonding. The basis weight of nonwoven fabrics is usually expressed in grams per square meter ($g/m^2$). For the present disclosure, a multilayered nonwoven web may be consolidated and bonded by hydroentanglement and/or needle punching, in addition to being consolidated and bonded by bonds obtained by heat and/or compression (including ultrasonic bonding), e.g. in order to impart improved loft to the nonwoven web. Carded webs are formed of short, so-called staple fibers. They are typically formed into a layer of fibers and subsequently consolidated into a nonwoven web, for example by applying a binder to the fibers (as described above), by autogenously bonding the fibers together with heat and/or by intertwining the fibers by known processes such as hydroentangling or needle-punching. The carded fibers may also be bonded together, e.g. by one or more patterns of bonds and bond impressions created through localized compression and/or application of heat or ultrasonic energy, or a combination thereof.

As used herein, a "pantiliner" and a "sanitary napkin" generally have two end regions and a middle region (i.e. a crotch region). The pantiliner and the sanitary napkin have a body-facing surface and a garment facing surface. The size and shape of the absorbent structure positioned between the topsheet and the backsheet can be altered to meet absorbent capacity requirements, and to provide comfort to the wearer. The garment facing surface of the pantiliner and of the sanitary napkin can have thereon pressure sensitive adhesive for affixing to a wearer's undergarments. Typically, such adhesive is covered with a release strip which is removed before affixing to the undergarment. Pantiliners can also be provided with lateral extensions known commonly in the art as "flaps" or "wings" intended to extend over and cover the panty elastics in the crotch region of the user's undergarment. However, wings are normally not used with pantiliners but are more often used in sanitary napkins. Sanitary napkins and pantiliners of the present disclosure comprise barrier leg cuffs.

In more details, FIG. 1 is a plan view of an example diaper 20, in a flat-out state, with portions of the diaper being cut-away to more clearly show the construction of the diaper 20. As said, this diaper 20 is shown for illustration purpose only as the structure of the present disclosure may be comprised in a wide variety of diapers or other absorbent articles, such as pants.

As shown in FIG. 1, the absorbent article, here a diaper, can comprise a liquid pervious topsheet 24, a liquid impervious backsheet 26, an absorbent core 28 which is positioned between the topsheet 24 and the backsheet 26. The absorbent core 28 can absorb and contain liquid received by the absorbent article and may comprise absorbent materials 60, such as superabsorbent polymers 66 and/or cellulose fibers, as well as other absorbent and non-absorbent materials commonly used in absorbent articles (e.g. thermoplastic adhesives immobilizing the superabsorbent polymer particles). The absorbent article of the present disclosure, such as the diaper 20 illustrated in FIG. 1, may optionally also include an acquisition system with an upper 52 and lower 54 acquisition layer.

The diaper also comprises barrier leg cuffs 34 and may further comprise elasticized leg cuffs 32. Moreover, the absorbent article may comprise a fastening system, such as an adhesive fastening system or a hook and loop fastening member, which can comprise tape tabs 42, such as adhesive tape tabs or tape tabs comprising hook elements, cooperating with a landing zone 44 (e.g. a nonwoven web providing loops in a hook and loop fastening system).

The diaper or pant, such as the diaper 20 shown in FIG. 1 can be notionally divided in a first waist region 36, a second waist region 38 opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper (the same applies to for the transversal centerline and longitudinal line of other absorbent articles of the present disclosure). The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20. The crotch region, the first and the second waist region each constitutes ⅓ of the absorbent article along the longitudinal centerline.

Further, the diaper may comprise other elements, such as a back waist feature, which may be non-elastic or elastic, and a front waist feature, which may be non-elastic or elastic, a lotion applied onto the wearer-facing surface of the topsheet, back ears 40, and/or front ears 46.

The front and/or back ears 40, 46 may be separate components attached to the diaper or may instead be continuous with portions of the topsheet and/or backsheet—and/or even portions of the absorbent core—such that these portions form all or a part of the front and/or back ears 40, 46. Also combinations of the aforementioned are possible, such that the front and/or back ears 40, 46 are formed by portions of the topsheet and/or backsheet while additional materials are attached to form the overall front and/or back ears 40, 46. The front and/or back ears may be elastic or non-elastic.

The topsheet 24, the backsheet 26, and the absorbent core 28 may be assembled in a variety of well known configurations, in particular by gluing, heat embossing, ultrasonic bonding or combinations thereof. Example diaper configurations are described generally in U.S. Pat. Nos. 3,860,003; 5,221,274; 5,554,145; 5,569,234; 5,580,411; and 6,004,306.

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polypropylene or bicomponent PE/PP fibers or mixtures thereof), or a combination of natural and synthetic fibers. The topsheet may have one or more layers. The topsheet may be apertured or non-apertured, and may have any suitable three-dimensional features, and/or may have a plurality of embossments (e.g., a bond pattern). Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm Other suitable backsheet materials may include breathable materials which permit vapors to escape from the absorbent article, while still preventing, or at least inhibiting, bodily exudates from passing through the backsheet.

The backsheet may comprise a backsheet outer cover material (sometimes referred to as a backsheet nonwoven) 40. The backsheet outer cover material may comprise one or more nonwoven materials joined to a backsheet film 28 and that covers the backsheet 28. The outer cover material 40 may form the garment-facing surface of the backsheet so that film is not present on the garment-facing surface. The backsheet outer cover material 40 may comprise a bond pattern, apertures, and/or three-dimensional features.

As set out in the background section above, PET resin which has been produced with a catalyst other than antimony generally leads to a resin with a yellowish color. Therefore, while the inventors found it desirable to use PET resin which has been produced with a catalyst other than antimony, they realized that the yellow color will not be accepted by consumers.

When considering the known processes described above in the background section, which attempt to avoid the yellowing of the PET resin with other catalyst systems, it has been found that these processes typically apply substances such as inks, or phosphorous compounds. The presence of such substances in the PET resin has been identified as not being desirable, as they may give rise to health and environment related concerns as well, so replacing antimony with another substance that might be considered as problematic, has been found to be non-preferred.

The inventors have found that a nonwoven material comprising PET can be used in absorbent articles despite the yellowish color of the PET resin having less than 150 ppm of antimony, if one or more other layers are covering the nonwoven material, both towards the wearer-facing surface and towards the garment-facing surface of the absorbent article. The one or more other layers overlay the nonwoven material such that the nonwoven material neither forms the wearer-facing surface nor the garment-facing surface of the absorbent article. The one or more other layers may have a certain minimum opacity such that the yellowish color is not apparent from the wearer-facing surface and the garment-facing surface of the absorbent article. As is set out below, the minimum opacity for the cover layer(s) has been found to be relatively low in order to be able to sufficiently cover up the yellowish color of the PET resin with less than 150 ppm of antimony.

PET fibers formed from PET resin made by a process not using antimony as a catalyst have been subjected to color tests, determining the a* and b* value as well as the L* value of these fibers, see examples below. The same fibers have been color tested by covering the fibers with materials, which are typically used as topsheet or backsheet materials in an absorbent article. The a*, b* and L* values have been determined through the materials overlaying the PET fibers. It has been found that even topsheet or backsheet materials having a relatively low opacity lead to a significant change of the a*, b* and L* values. I.e. the yellowish look of the PET fibers was no longer visible, or was only visible to a significantly lower extent.

It has been found that even when the PET fibers formed from PET resin made by a process not using antimony as a catalyst are covered by an apertured nonwoven fabric (which may form the topsheet of the absorbent article), the yellowish color of the PET fibers is significantly reduced.

The opacity of the one or more layers covering the nonwoven material with the PET fibers can be increased, e.g. by increasing the basis weight of these layers, by using fibers with smaller diameter, such as materials comprising meltblown fibers and/or nanofibers, or by using film layers instead of nonwoven webs.

If more than one layer is covering the nonwoven material comprising PET with less than 150 ppm antimony, the opacity referred to herein is the combined opacity of these layers. Hence, opacity is determined by measuring the combined layers.

The nonwoven material comprising PET with less than 150 ppm antimony may be provided between the topsheet and the absorbent core. It may be in direct contact with the topsheet of the absorbent article.

For example, the absorbent article may comprise an acquisition system provided between the absorbent core and the topsheet and the nonwoven material comprising PET with less than 150 ppm antimony may be comprised by the acquisition system, such as forming an upper layer of an acquisition system which is in direct contact with the topsheet. The nonwoven material comprising PET with less than 150 ppm of antimony comprised by the acquisition system may be in the form of a nonwoven web.

Alternatively, or in addition to being provided between the topsheet and the absorbent core, the nonwoven material comprising PET with less than 150 ppm antimony may also be provided between the backsheet and the absorbent core of the absorbent article.

Suitable nonwoven material comprising the PET with less than 150 ppm of antimony comprise nonwoven webs comprising spunlaid layers, meltblown layers, layers of nanofibers or combinations of such layers. Generally, the diameter of spunlaid fibers is larger compared to the diameter of meltblown fibers, which in turn have a somewhat larger diameter than nanofibers. Spunlaid fibers typically have a diameter of 8 µm to 40 µm; meltblown fibers have a diameter of 0.5 µm to ≤8 µm, while nanofibers generally have a diameter of 0.01 µm to 1.5 µm. Nanofibers can be made by different processes, including advanced meltblown as disclosed in U.S. Pat. No. 7,922,943B2, melt film fibrillation as disclosed in U.S. Pat. No. 7,931,457B2 or electrospinning as disclosed in U.S. Pat. No. 6,616,435B2. The spunlaid fibers may also have non-circular cross-sections, in which case the major and minor axes of the cross-sectional shape have lengths in the range from 8 µm to 40 µm.

The nonwoven material, such as a nonwoven web, may also be made of carded fibers (so-called staple fibers) or the nonwoven material may be a multilayer nonwoven web comprising one or more layers of carded fibers and one or more layers of spunlaid, meltblown and/or nano fibers. Examples include, but are not limited to SMS multilayer nonwoven webs, comprising a spunlaid, a melt-blown and a further layer. Another suitable multilayer nonwoven webs of the present disclosure comprise webs having a SMMS-structure (two outer spunlaid layers and two inner melt-blown layers) or a SMMMS-structure (two outer spunlaid layers with three inner meltblown layers). Other suitable multilayered nonwoven webs have a SNS structure, comprising a spunlaid, a nanofiber and a further spunlaid layer, or SMNS webs, comprising a spunlaid, a meltblown, a nanofiber and a further spunlaid layer.

Nonwoven webs having spunlaid fibers forming the outer surfaces of the nonwoven web tend to have better resistance to fuzz, i.e. the fibers exposed to the surface of the nonwoven web are not as easily abraded and twitched out of the nonwoven web as fine fibers with smaller diameters (such as meltblown fibers or nanofibers).

On the other hand, nonwoven webs, wherein the outer surface of the web is formed of a meltblown fibers or nanofibers may be able to provide a more uniform appearance on the outer surface at a given basis weight of the fiber layer as the fibers have a considerably smaller diameter.

The PET having less than 150 ppm of antimony may also be free of dyes, pigments, hues and optical brighteners, as such compounds include substances which have recently also gained increased attention with regard to potential adverse effects for the human health and the environment. The same applies to phosphorous compounds which are comprised by some antimony-free PET resins previously suggested, where a phosphorus stabilizer is used in the PET resin manufacturing process to reduce the yellowish color. Also, some antimony-free PET resins described in the art may comprise trimellitic anhydride, and triethyl phosphonoacetate (TEPA) and the presence of these compounds is not desirable for use of the PET resin in absorbent articles.

The nonwoven material (as a whole) comprising PET with less than 150 ppm antimony may be free of dyes, pigments, hues and optical brighteners, and/or may be free of phosphorous substances, and/or may be free of trimellitic anhydride, and triethyl phosphonoacetate.

The nonwoven material, comprising PET having less than 150 ppm of antimony, comprises at least 10%, by weight of the nonwoven material, of such PET. The PET may be comprised by the fibers of the nonwoven material. The nonwoven material may comprise at least 30%, or at least 50%, or at least 70%, or 100%, by weight of the nonwoven material, of PET having less than 150 ppm of antimony. If the nonwoven material comprises less than 100% of PET, the nonwoven may further comprise fibers formed of a thermoplastic material other than PET, such as polyolefin, polyamide, or specifically polypropylene (PP), polyethylene (PE), poly-lactic acid (PLA), Nylon 6-6 as well as combinations thereof (such as blends and copolymers).

The nonwoven material may not comprise any PET having more than 150 ppm, or more than 100 ppm, or more than 75 ppm, or more than 50 ppm, or more than 10 ppm of antimony, or may not comprise any PET which is not completely antimony-free (i.e. zero ppm).

The absorbent article may not comprise any PET having more than 150 ppm, or more than 100 ppm, or more than 75 ppm, or more than 50 ppm, or more than 10 ppm of antimony, or may not comprise any PET which is not completely antimony-free (i.e. zero ppm).

The PET having less than 150 ppm of antimony may be provided as homopolymer of PET, as copolymer (co-PET) or as a combination thereof. A combination thereof may include a mixture of fibers comprising homopolymer of PET and fibers comprising co-PET.

PET consists of polymerized units of the monomer ethylene terephthalate, with repeating $(C_{10}H_8O_4)$ units.

In co-PET, for example, cyclohexane dimethanol (CHDM) can be added to the polymer backbone in place of ethylene glycol. Since this building block is much larger (6 additional carbon atoms) than the ethylene glycol unit it replaces, it does not fit in with the neighboring chains the way an ethylene glycol unit would. This interferes with crystallization and lowers the polymer's melting temperature. In general, such PET is known as PETG or PET-G (Polyethylene terephthalate glycol-modified; Eastman Chemical, SK Chemicals, and Artenius Italia are some PETG manufacturers).

Another common modifier for obtaining co-PET is isophthalic acid, replacing some of the 1,4-(para-) linked terephthalate units. The 1,2-(ortho-) or 1,3-(meta-) linkage produces an angle in the chain, which also disturbs crystallinity.

All of the fibers of the nonwoven material of the present disclosure may be formed from thermoplastic material, such as polyolefin, polyamide or specifically polypropylene (PP), polyethylene (PE), poly-lactic acid (PLA), polyethylene terephthalate (PET), Nylon 6-6 as well as combinations thereof (such as blends and copolymers), in addition to comprising staple fibers comprising PET with less than 150 ppm of antimony. However, the nonwoven material may, in addition to the at least 10%, by weight of the nonwoven material, of PET with less than 150 ppm, also comprise fibers made of non-thermoplastic fibers, such as natural fibers. Such natural fibers include, for example, cotton or cellulose fibers. The natural fibers may be provided as one or more separate layers in the nonwoven material, and/or they be mixed with the other, non-natural, fibers.

Generally, resins including PP may be particularly useful because of PP's relatively low cost, low density and surface friction properties of fibers formed from it (i.e., they have a relatively smooth, slippery tactile feel), as well as their good mechanical properties. Resins including PE may also be desirable because of polyethylene's relative softness/pliability and even more smooth/slippery surface friction properties. Relative each other, PP currently has a lower cost and fibers formed from it have a greater tensile strength, while PE currently has a greater cost and fibers formed from it have a lower tensile strength but greater pliability and a more smooth/slippery feel. Multicomponent fibers from PP and PE are desirable for as they combine the good softness properties of PP and the good mechanical properties of PE.

The thermoplastic polymer suitable for the fibers comprised by the nonwoven material, comprising PET with less than 150 ppm of antimony, may also be thermoplastic starch. As used herein, "thermoplastic starch" or "TPS" means a native starch or a starch derivative that has been rendered destructured and thermoplastic by treatment with one or more plasticizers, with at least one starch plasticizer still remaining. Thermoplastic starch compositions are well known and disclosed in several patents, for example: U.S. Pat. Nos. 5,280,055; 5,314,934; 5,362,777; 5,844,023; 6,214,907; 6,242,102; 6,096,809; 6,218,321; 6,235,815; 6,235,816; and 6,231,970.

The nonwoven material may have any basis weight. However, relatively higher basis weight, while having relatively greater apparent caliper and loft, also has relatively greater cost.

The basis weight for the nonwoven material, such as a nonwoven web, comprising PET with less than 150 ppm of antimony may be 200 $g/m^2$ or less, or may be from 5 $g/m^2$ to 120 $g/m^2$, or from 10 $g/m^2$ to 100 $g/m^2$, or from 15 $g/m^2$ to 80 $g/m^2$, or from 30 $g/m^2$ to 60 $g/m^2$.

It may generally be desirable to have nonwoven material with relatively homogeneous distribution of fibers, i.e. webs wherein the fibers have been laid down homogeneously, especially for nonwoven materials with relatively low basis weight. If the nonwoven material comprises other fibers or materials (such as, e.g., binder) in addition to the fibers comprising PET with less than 150 ppm of antimony, the fibers comprising PET with less than 150 ppm of antimony may be homogeneously distributed within the nonwoven material.

The nonwoven material, comprising PET with less than 150 ppm of antimony, may be a carded nonwoven web. The fibers of the carded nonwoven fibrous web(s) are staple fibers. The carded nonwoven web comprising PET with less than 150 ppm of antimony, may comprise a binder, such as a liquid latex binder which has been cured after application onto the fibers to solidify. Alternatively, the carded nonwoven web comprising PET with less than 150 ppm of antimony may not comprise a liquid binder which has been cured to solidify.

For example, a carded nonwoven web comprising the PET having less than 150 ppm of antimony may comprise at least 50%, or from 60% to 90%, or from 60% to 80% by weight of the carded nonwoven web, of staple fibers and at least 10%, or from 10% to 40%, or from 20% to 40%, by weight of the carded nonwoven web, of a latex binder. Staple fibers are short fibers. They may have a length of from 10 mm to 120 mm, or from 25 mm to 80 mm, or from 25 mm to 60 mm. The staple fibers may be straight or, alternatively, may have two-dimensional or three-dimensional crimp. Crimped staple fibers can improve the resiliency of the nonwoven web, which is generally desirable when the nonwoven web is comprised by an acquisition system of the absorbent article.

In another example, a carded nonwoven web comprising the PET having less than 150 ppm of antimony may comprise staple fibers which have been autogeneously bonded to each other, e.g. by subjecting the carded fibers to a through-air bonding process. Such carded nonwoven webs will typically not comprise a liquid binder (such as a latex binder) which has been cured to solidify after application onto the fibers.

Carding is a mechanical process using staple fibers. To obtain staple fibers, the fibers are first spun, cut to a few centimeters length. The cut fibers are combed into a layer of fiber material by a carding machine, such as a rotating drum or series of drums covered in fine wires or teeth.

In contrast to carded nonwoven webs, spunlaid and meltblown nonwoven webs are typically made in one continuous process. Fibers are spun and then directly dispersed into a web by deflectors or directed with air streams. The fibers of a spunlaid or meltblown nonwoven are considerably longer compared to staple fibers.

The fibers useful for the nonwoven material comprising PET having less than 150 ppm of antimony content, are monocomponent fibers as well as multicomponent fibers. Suitable multicomponent fibers are bicomponent fibers, such as core/sheath bicomponent fibers and side-by-side bicomponent fibers. The core/sheath bicomponent fibers may be concentric or eccentric fibers.

If the fibers of the nonwoven material comprising PET with less than 150 ppm of antimony, comprise core/sheath bicomponent fibers, it is desirable that the sheath is made of a polymer which has a melting point below the melting point of the polymer which forms the core component. If such bicomponent fibers are subjected to through-air bonding or calendar bonding, the temperature of the through air bonding process or the bonding calendar is typically selected such that the polymer of the sheath component is at least partially transferred to a molten state (or partly molten state, or molten to a state where the fiber surface becomes sufficiently tacky) such that the fibers bond together while the core component of the bicomponent fiber remains substantially unaffected.

If side-by-side bicomponent fibers are used, the polymers forming the first and second component may also have different melting points. If such bicomponent fibers are subjected to through-air bonding or calendar bonding, the temperature of the through air bonding process or the bonding calendar is selected such that the polymer of the component having the lower melting point is molten is at least partially transferred to a molten state (or partly molten state, or to a state where the fiber surface becomes sufficiently tacky) such that the fibers bond together while the polymer of the component having the higher melting point remains substantially unaffected.

The shape of the fibers of the nonwoven web comprising PET with less than 150 ppm of antimony, may be round (i.e. fibers having a circular cross-section). Alternatively, the fibers may have non-round shape, such as multilobal fibers (e.g. trilobal fibers), flat fibers ("ribbon-like" cross-section), rhomboid fibers or triangular fibers. In multilobal fibers, a central section is encircled by a multiplicity of lobes. E.g. in a trilobal fiber, the central section is encircled by three lobes. The nonwoven material comprising PET with less than 150 ppm of antimony may also comprise a mixture of fibers having different shapes, such as a mixture of round and multilobal fibers.

The fibers of the nonwoven material comprising PET with less than 150 ppm of antimony may be solid or hollow. Alternatively, the nonwoven web comprising the PET with less than 150 ppm of antimony have comprise a mixture of solid and hollow fibers. The solid fibers may or may not have a different shape than the hollow fibers.

Test Methods

Measurement of a*, b*, L* and Delta E* Values

The measurement is based on the CIE L* a* b* color system (CIELAB). L*, a* and b* may be measured using a 0.deg. illumination/45.deg. detection, circumferential optical geometry, spectrophotometer with a computer interface such as the HunterLab LabScan® XE running Universal Software (available from Hunter Associates Laboratory Inc., Reston, Va.). The HunterLab LabScan® XE is equipped with a Port Down Stand, which enables measurement of the sample from a straight-down angle. Instrument calibration and measurements are to be made using the standard protocol by the vendor. All testing is performed in a room maintained at about 23° C.±2° C. and about 50%±2% relative humidity.

Configure the spectrophotometer for the L*, a*, b* color value scale, D65 illuminant, 10.deg. standard observer, with UV filter set to nominal. Standardize the instrument according to the manufacturer's procedures using the 1.20 inch port size and 1.00 inch area view.

To obtain the specimen of the nonwoven material comprising PET with less than 150 ppm of antimony, eight pieces of the nonwoven material, each being at least 31 mm by 31 mm, are cut and stacked up one on top of the other. The eight-layer specimen is measured for L*, a*, b* values. The specimen needs to have a sample size of at least 31 mm by 31 mm. In case loose, staple fibers are to be measured the fiber amount used within the 1.2 inch port area needs to at least 0.1 g (equivalent to eight layers of about 20 gsm), max. 1.7 g (equivalent to eight layers of 300 gsm).

When, in the absorbent article, the nonwoven material is covered by only one first layer layer towards the wearer-facing surface of the article, then this one first cover layer is placed (as single layer) on top of the nonwoven material (web, or alternatively, "batt" of loose fibers) to cover it. When, in the absorbent article, the nonwoven material is covered by more than one first cover layer, then all these first cover layers are placed on top of the nonwoven material (web, or alternatively, "batt" of loose fibers) to cover it. The order of these first cover layers is the same as it is in the absorbent article.

The same procedure is followed for the measurement of the one or more second cover layers covering the nonwoven web towards the garment-facing surface of the absorbent article. L*, a*, b* values are then measured for the nonwoven material (web, or alternatively, "batt" of loose fibers) covered by the respective one or more layers and delta E* value is calculated.

If any materials need to be removed from an absorbent article prior to the measurement, it may be necessary to use a cryogenic freeze spray (e.g. CytoFreeze, Control Company, TX) to remove the specimen from the product. For the nonwoven web comprising the PET resin with less than 150 ppm of antimony, cut eight pieces of at least 31 mm by 31 mm. If the material in the absorbent article is not sufficiently large to cut eight pieces of 31 mm by 31 mm, then several substantially identical absorbent articles are taken and a piece of at least 31 mm by 31 mm is cut from each article and the pieces are put one on top of the other to obtain a specimen of 8 layers. For the one or more layer(s) covering the nonwoven material, cut a piece of at least 31 mm by 31 mm Precondition samples at about 23° C.±2° C. and about 50%±2% relative humidity for 2 hours prior to testing.

Place the specimen on the spectrophotometer. The specimen should completely cover the port. For the measurements where one or more layer(s) are covering the nonwoven material the layer facing the wearer/facing the garment, respectively, is directed toward the port of the spectrophotometer.

A total of three substantially identical samples are analyzed and their L*, a*, b* results recorded. Calculate and report the average values and standard deviation for the material measurements to the nearest 0.01%.

Record the averaged values as $L^*_1$, $a^*_1$ and $b^*_1$ for the specimen the nonwoven material comprising the PET with less than 150 ppm antimony taken alone, and the averaged values as $L^*_2$, $a^*_2$ and $b^*_2$ for the nonwoven material when covered with the one or more cover layer. Calculate and report the color difference (delta E*) between the nonwoven material taken alone, and the nonwoven material covered with the one or more cover layers, using the following equation:

$$\text{delta } E^* = \sqrt{(L^*_2 - L^*_1)^2 + (a^*_2 - a^*_1)^2 + (b^*_2 - b^*_1)^2}$$

Opacity Measurement Method

The opacity of a material is the degree to which light is blocked by that material. A higher opacity value indicates a higher degree of light block by the material. Opacity may be measured using a 0.deg. illumination/45.deg. detection, circumferential optical geometry, spectrophotometer with a computer interface such as the HunterLab LabScan® XE running Universal Software (available from Hunter Associates Laboratory Inc., Reston, Va.). Instrument calibration and measurements are made using the standard white and black calibration plates provided by the vendor. All testing is performed in a room maintained at about 23° C.±2° C. and about 50%±2% relative humidity. Configure the spectrophotometer for the XYZ color scale, D65 illuminant, 10.deg. standard observer, with UV filter set to nominal. Standardize the instrument according to the manufacturer's procedures using the 1.20 inch port size and 1.00 inch area view. After calibration, set the software to the Y opacity procedure.

To obtain the specimen, the single first cover layer covering the nonwoven material, comprising PET with less than 150 ppm of antimony, towards the wearer-facing surface is taken alone, if the nonwoven material is only covered by that single layer in the absorbent product. If the nonwoven material is covered by more than one first cover layer, then all the layers covering the nonwoven material in the absorbent article are taken in combination for the measurement. The same rationale applies for the second cover layer(s) covering the nonwoven web towards the garment-facing surface. If the layer(s) need(s) to be removed from an absorbent article, it may be necessary to use a cryogenic freeze spray (e.g. CytoFreeze, Control Company, TX) to remove the specimen from the product. Cut a piece 50.8 mm by 50.8 mm centered at each site identified above. Precondition samples at about 23° C.±2° C. and about 50%±2% relative humidity for 2 hours prior to testing.

Place the specimen over the measurement port. The specimen should completely cover the port with the first outer surface directed toward the port. Cover the specimen with the white standard plate. Take a reading, then remove the white tile and replace it with black standard tile without moving the specimen. Obtain a second reading, and calculate the opacity as follows:

Opacity=[Y value (black backing)/Y value (white backing)]×100%

A total of five substantially identical samples are analyzed and their opacity results recorded. Calculate and report the average opacity and standard deviation for the material measurements to the nearest 0.01%.

L*, a* and b* Values and Opacity Measurement for Absorbent Articles Comprising Materials which are Substantially Inhomogeneous If the nonwoven material comprising the PET resin with less than 150 ppm of antimony and/or any of the one or more first and/or second cover layers covering the nonwoven web towards the wearer-facing surface or the garment-facing surface, respectively, is substantially inhomogeneous, e.g. due to graphics printed on these materials, then the following procedure is to be followed:

Several, randomly chosen locations on a (first) absorbent article are selected for taking the test specimen. The number of different locations chosen, depends on the degree of variation on the materials to be tested. Generally, the chose locations may encompass those, where the skilled person expects relatively high as well as relatively low opacity values and a* and b* values deviating substantially from zero.

In total, three substantially identical absorbent articles are taken and test specimen for the second and third absorbent article are taken from the same locations as those identified for the first absorbent article. For all three absorbent articles, the test specimens are taken and measured as set out above for opacity and L*, a*, b* and delta E* measurement. The values for each set of three substantially identical specimens (i.e. those taken from the same location in each article) are taken and their average value and standard deviation is reported as set out above.

To be within the ranges for L*, a*, and b* values, delta E* values and opacity as set out herein above and below, the value obtained for each measured specimen location within the absorbent article has to be within a given range as described herein, i.e. it is not sufficient if the values in only one or a couple of locations are with the range. However, locations are only those regions of the absorbent article where the nonwoven material with PET resin of less than 150 ppm of antimony provided. I.e. regions where the one or more layers that cover the nonwoven web are also provided without the nonwoven material underneath are not to be taken into consideration when selecting the locations for the measurements.

Measurement of Aperture Size and Open Area of an Apertured Topsheet

Apertures (also referred to as "effective apertures" below) are defined as having a gray level of 18 or less on a standard gray level scale of 0-255, under the image acquisition parameters described below.

The aperture size and open area are determined by the following procedure using the image analysis described below. The procedure has three principal steps: image acquisition, i.e., obtaining representative images of areas on the surface of the topsheet; image measurement, i.e., measuring the percentage open area of an image and of individual apertures and their perimeters; and data analysis, i.e., exporting the percentage open area, individual aperture area, and perimeter measurements to a spreadsheet where frequency distributions, sum of area distributions, and hydraulic radius computations are made.

An image analysis system having a frame grabber board, microscope, camera and image analysis software is utilized. A model DT2855 frame grabber board available from Data Translation of Marlboro, Mass. (or similar) is provided. A VH5900 monitor microscope (or equivalent), a video camera, having aVH50 lens with a contact type illumination head available from the Keyence Company of Fair Lawn, N.J. are also provided and used to acquire an image to be saved to computer file. The Keyence microscope acquires the image and the frame grabber board converts the analog signal of this image into computer readable digital format. The image is saved to computer file and measured using suitable software such as the Optimas Image Analysis software, version 3.1, available from the BioScan Company of Edmaons, Wash. (or similar).

The image acquisition step, noted above requires 10 different regions from a representative sample of material to be tested. Each region is rectangular, measuring about 5.8 millimeters by 4.2 millimeters. The sample is placed on a black mat board to increase the contrast between the apertures and the portion of the sample which defines the apertures. The mean gray level and standard deviation of the black mat board were 16 and 4, respectively.

Images are acquired with room lights off using the Keyence monitor microscope mounted on a copystand directly above the sample. The Keyence light source illuminating the sample is adjusted and monitored with the Optimas software to measure the mean gray level and standard deviation of a 0.3 density wedge on a Kodak Gray Scale available from Eastman Kodak Company of Rochester, N.Y. The control of Keyence light source is adjusted so that the mean gray level of the illuminated wedge is 111+1 and the standard deviation is 10+1. All images were acquired during a single time period, and the Keyence light source is monitored by measuring the mean gray level and standard deviation of the wedge throughout the image acquisition process.

In measuring an individual aperture, only the effective aperture size is of interest. Measuring the effective aperture size quantifies the aperture size intended to contribute to the porosity of the material, and account for contributions of fibers and fiber bundles which traverse an area intended to be an aperture. An effective aperture is any hole through the material having a gray level less than or equal to 18 using image acquisition parameters as described herein. Thus, an intended aperture may be divided into plural effective apertures by traverse fibers.

The image analysis software is calibrated in millimeters by a ruler image acquired from the sample images. A 3 by 3 pixel averaging filter found in the Optimas 3.1 Image menu is applied to each saved image to reduce noise. The apertures are detected in the gray level range of 0 through 18. An aperture which is not fully contained within the 5.8 by 4.2 viewing area is not considered in the individual area and perimeter measurements. Therefore, area and perimeter averages and distributions are not affected by apertures which are not wholly contained within the field of view.

However, individual apertures which could not be fully viewed in the image are included in the percentage open area calculation. This difference occurs because the percent open area is simply the image of pixel ratios from 0 through 18 to the total number of pixels in the image. Areas having a gray level 19 or greater were not counted in the open area calculation.

The percentage open area for the average of 10 images for each material is measured using the Optimas Image Analysis software. The percentage open area is defined as the ratio of the number of pixels having a gray level from 0 through 18 to the total number of pixels for the image. The percentage open area is measured for each image representing one particular region from a sample. The percentage open area from each of the 10 individual images is then averaged to yield a percentage open area for the entire sample.

Deviations, size and frequency distributions of individual aperture areas and hydraulic radius computations (area divided by perimeter) for individual apertures are obtained using the spreadsheet.

Distributions of individual aperture area are also computed using the Excel spreadsheet. The apertures are sorted into bins of certain size ranges. The number of aperture areas falling into certain size ranges of interest is determined as well as the sum of the areas within each range. The ranges are set in increments of 0.05 mm$^2$. These areas are expressed as a percentage of the total open area of the sample. The frequency and sum of the area distributions are obtained by combining individual aperture measurements from all 10 images for each sample.

EXAMPLES

Example 1

L*, a* and b* values of a nonwoven material in the form of loose staple fiber of PET fibers having less than 10 ppm of antimony were tested in accordance with the test method set out above.

1.2 g of fibers were used as specimen. Fibers were a 50/50 mixture of 6 denier solid round fibers with 100% PET having less than 10 ppm of antimony and 9 denier solid round fibers with 100% PET having less than 10 ppm of antimony. Both types of stable fibers has length of 51 mm Fibers were semi-dull, i.e. they comprised between 0.15 and 0.35% of $TiO_2$.

Example 2

The 1.2 g specimen of Example 1 was covered with a nonwoven web (one layer of material only). The web had a basis weight of 12 g/m² and was a spunbonded material made of polypropylene (suitable as topsheet material in absorbent articles).

L*, a* and b* values of the loose staple fibers of Example 1 covered with the 12 g/m² spunbonded nonwoven web were measured. Delta E* between Example 1 taken along and loose fibers covered with the 12 g/m² spunbonded nonwoven web was calculated.

Separately, the opacity and L*, a* and b* values of the 12 g/m² spunbonded nonwoven web were measured without loose PET fibers underneath. Measurements were done with one layer of the nonwoven web only (i.e. not folded three times to obtain a 8-layer specimen).

Example 3

The 1.2 g specimen of Example 1 was covered with a nonwoven web (one layer of material only). The web had a basis weight of 11 g/m² and was a SMS nonwoven web (i.e. it had two outer spunbond layers with one meltblown layer in between). The 11 g/m² nonwoven web was made of polypropylene (suitable as outer cover nonwoven of a backsheet in absorbent articles). L*, a* and b* values of the loose staple fibers of Example 1 covered with the 11 g/m² SMS nonwoven web were measured. Delta E* between Example 1 taken along and loose fibers covered with the 11 g/m² SMS nonwoven web was calculated.

Separately, the opacity and L*, a* and b* values of the 11 g/m² SMS nonwoven web were measured without loose PET fibers underneath. Measurements were done with one layer of the nonwoven web only (i.e. not folded three times to obtain a 8-layer specimen).

Example 4

The 1.2 g specimen of Example 1 was covered with a nonwoven web (one layer of material only). The web had a basis weight of 20 g/m² and was an apertured nonwoven web made of bicomponent spunbond fibers. The bicomponent fibers were core/sheath bicomponent fibers made of polypropylene core component and polyethylene sheath component. (suitable as topsheet material in absorbent articles). The apertured nonwoven web had a total open area of 30% and an aperture size of 4.6 mm²

L*, a* and b* values of the loose staple fibers of Example 1 covered with the 20 g/m² apertured nonwoven web were measured. Delta E* between Example 1 taken along and loose fibers covered with the 20 g/m² apertured nonwoven web was calculated.

Separately, the opacity and L*, a* and b* values of the 20 g/m² apertured nonwoven web were measured without loose PET fibers underneath.

Table 1: Results of L*, a*, b* and opacity measurements for Examples 1-4

Loose PET fibers with less than 150 ppm antimony alone and for nonwoven cover material only (i.e. nonwoven material not covering the loose fibers)

|  | L* | a* | b* | Opacity [%] |
|---|---|---|---|---|
| Example 1 | 81.50 | −1.11 | 2.01 | — |
| Example 2 | 42.14 | 0.04 | −0.69 | 15 |
| Example 3 | 47.61 | 0.01 | −0.62 | 22 |
| Example 4 | 52.04 | 0.12 | −0.73 | 30 |

Table 2: Results of L*, a*, b* and delta E* measurements for Examples 2-4

Results for nonwoven material covering the loose PET fibers

|  | L* | a* | b* | delta E* |
|---|---|---|---|---|
| Example 2 | 88.66 | −0.99 | 1.64 | 7.2 |
| Example 3 | 89.06 | 0.99 | 1.77 | 7.6 |
| Example 4 | 87.70 | 0.96 | 1.15 | 6.2 |

An a* value of 0.0 and b* value of 0.0 indicates white. Values above or below 0 indicate a color (i.e. non-white).

Generally, a delta E* of 0.0 to 0.5 is basically unnoticeable; a delta E* of 0.5 to 1.0 is noticeable to the trained eye; a delta E* of 1.0 to 2.0 is recognized as a small color difference; a delta E* of 2.0 to 4.0 is a noticeable color difference; a delta E* of 4.0 to 5.0 is a significant color difference; and a delta E* of 5.0 or larger is recognized as a different color.

While the PET fibers with less than 10 ppm of antimony alone (Example 1) had a yellowish color that was well noticeable to the naked eye, as is reflected especially by the b* value, covering the fibers with a nonwoven (having no noticeable yellowish color on their own), led to a significant reduction of the yellowish color. Moreover, it has been found that even nonwovens having a relatively small percentage of opacity, worked well in covering up and concealing the yellowish color.

Nonwovens having a high percentage of opacity require a high basis weight for the material (that cover the material comprising PET with less than 150 ppm of antimony), adding cost and bulk to the absorbent article. Alternatively, or in addition, high opacity requires high levels of additives, such as titanium dioxide, also adding cost and reducing processability when manufacturing the nonwoven material. Hence, being able to significantly reducing the yellowish look by using cover layers having relatively low opacity is desirable.

Also, even apertured nonwovens have been found to work well for covering and concealing the yellowish color of the material comprising PET with less than 150 ppm of antimony. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the present disclosure. It is therefore intended to cover in the appended claims all such changes and modifications that are within the scope of the present disclosure.

What is claimed is:

1. An absorbent article comprising a topsheet forming a wearer-facing surface of the absorbent article, a backsheet forming a garment-facing surface of the absorbent article, and an absorbent core interposed between the topsheet and the backsheet,
   wherein the absorbent article comprises a nonwoven material, the nonwoven material:
      comprising at least 10%, by weight of the nonwoven material, of polyethylene terephthalate (PET), the PET comprising less than 150 ppm of antimony;
      having an a* value unequal zero;
      having a b* value unequal zero;
      being covered by one or more first cover layer(s) towards the wearer-facing surface of the absorbent article, the one or more first cover layer(s) comprising the topsheet, such that the nonwoven material does not form the wearer-facing surface of the absorbent article, wherein a delta E* value between the nonwoven material alone and the nonwoven material being covered by the one or more first cover layer(s), is at least 1.0; and
      being covered by one or more second cover layer(s) towards the garment-facing surface of the absorbent article, the one or more second cover layer(s) comprising the backsheet, such that the nonwoven material does not form the garment-facing surface of the absorbent article, wherein the delta E* value between the nonwoven material alone and the nonwoven material being covered by the one or more second cover layer(s), is at least 1.0.

2. The absorbent article of claim 1, wherein the a* value of the nonwoven material is less than −0.6.

3. The absorbent article of claim 1, wherein the b* value of the nonwoven material is higher than 1.5.

4. The absorbent article of claim 1, wherein
   the one or more first cover layer(s) have an opacity of at least 10%, wherein, for more than one first cover layer, the opacity is the combined opacity of the one or more first cover layer(s) covering the nonwoven material towards the wearer-facing surface, and
   the one or more second cover layer(s) have an opacity of at least 10%, wherein, for more than one second cover layer, the opacity is the combined opacity of the one or more second cover layer(s) covering the nonwoven material towards the garment-facing surface.

5. The absorbent article of claim 1, wherein the nonwoven material is provided between the topsheet and the absorbent core.

6. The absorbent article of claim 5, wherein the absorbent article comprises an acquisition layer which is provided between the absorbent core and the topsheet, and wherein the nonwoven material is comprised by the acquisition layer.

7. The absorbent article of claim 1, wherein the nonwoven material is in direct contact with the topsheet.

8. The absorbent article of claim 1, wherein the nonwoven material is provided between the backsheet and the absorbent core.

9. The absorbent article of claim 1, wherein the PET is provided as homopolymer, copolymer (co-PET), or a combination thereof.

10. The absorbent article of claim 1, wherein the nonwoven material comprises monocomponent fibers and the PET is comprised by monocomponent fibers.

11. The absorbent article of claim 1, wherein the PET comprised by the nonwoven material has less than 100 ppm of antimony.

12. The absorbent article of claim 1, wherein the PET does not comprise any of the following: dyes, pigments, hues and optical brighteners.

13. The absorbent article of claim 1, wherein the PET does not comprise a phosphorous compound.

14. The absorbent article of claim 1, wherein the absorbent core comprises a combination of cellulose fibers and superabsorbent polymer particles, and the absorbent core comprises areas which are free of cellulose fibers and superabsorbent polymer particles, wherein the areas are elongated areas having a length of from 20% and 80% by total longitudinal dimension of the absorbent article.

15. An absorbent article comprising a topsheet forming a wearer-facing surface of the absorbent article, a backsheet forming a garment-facing surface of the absorbent article, and an absorbent core interposed between the topsheet and the backsheet,
   wherein the absorbent article comprises a nonwoven material, the nonwoven material:
      comprising at least 10%, by weight of the nonwoven material, of polyethylene terephthalate (PET), the PET comprising less than 150 ppm of antimony, wherein the PET does not comprise any of the following: dyes, pigments, hues, optical brighteners, or a phosphorous compound;
      having an a* value unequal zero;
      having a b* value unequal zero;
      being covered by one or more first cover layer(s) towards the wearer-facing surface of the absorbent article, the one or more first cover layer(s) comprising the topsheet, such that the nonwoven material does not form the wearer-facing surface of the absorbent article, wherein a delta E* value between the nonwoven material alone and the nonwoven material being covered by the one or more first cover layer(s), is at least 1.0; and
      being covered by one or more second cover layer(s) towards the garment-facing surface of the absorbent article, the one or more second cover layer(s) comprising the backsheet, such that the nonwoven material does not form the garment-facing surface of the absorbent article, wherein the delta E* value between the nonwoven material alone and the nonwoven material being covered by the one or more second cover layer(s), is at least 1.0.

16. An absorbent article comprising a topsheet forming a wearer-facing surface of the absorbent article, a backsheet forming a garment-facing surface of the absorbent article, and an absorbent core interposed between the topsheet and the backsheet, wherein the absorbent article comprises a nonwoven material, the nonwoven material:
comprising at least 10%, by weight of the nonwoven material, of polyethylene terephthalate (PET), the PET comprising less than 150 ppm of antimony;
having an a* value unequal zero;
having a b* value unequal zero;
being covered by one or more first cover layer(s) towards the wearer-facing surface of the absorbent article, the one or more first cover layer(s) comprising the topsheet, such that the nonwoven material does not form the wearer-facing surface of the absorbent article;
being covered by one or more second cover layer(s) towards the garment-facing surface of the absorbent article, the one or more second cover layer(s) comprising the backsheet, such that the nonwoven material does not form the garment-facing surface of the absorbent article;
wherein a delta E* value between the nonwoven material alone and the nonwoven material being covered by the one or more first cover layer(s), is at least 1.0, and not more than 10; and
wherein the delta E* value between the nonwoven material alone and the nonwoven material being covered by the one or more second cover layer(s), is at least 1.0, and not more than 10.

17. The absorbent article of claim 16, wherein the a* value of the nonwoven material is less than −0.6.

18. The absorbent article of claim 16, wherein the b* value of the nonwoven material is higher than 1.5.

* * * * *